United States Patent [19]

Hartman

[11] 4,416,882

[45] Nov. 22, 1983

[54] DI(ALKYLAMINO) DERIVATIVES OF CHLORONITROPYRAZINES USEFUL AS ADJUNCTS TO RADIATION THERAPY

[75] Inventor: George D. Hartman, Lansdale, Pa.

[73] Assignee: Merck & Co., Inc., Rahway, N.J.

[21] Appl. No.: 399,503

[22] Filed: Jul. 19, 1982

Related U.S. Application Data

[63] Continuation-in-part of Ser. No. 194,091, Oct. 6, 1980, abandoned.

[51] Int. Cl.³ ................. C07D 241/16; A61K 31/495
[52] U.S. Cl. ..................................... 424/250; 544/407; 544/409
[58] Field of Search ................. 544/409, 407; 424/250

[56] References Cited

U.S. PATENT DOCUMENTS

| | | | |
|---|---|---|---|
| 2,944,061 | 6/1960 | Jacob et al. | 548/338 |
| 3,660,397 | 5/1972 | Jones et al. | 544/350 |
| 3,772,313 | 11/1973 | Gizycki et al. | 544/407 |

OTHER PUBLICATIONS

Ainsworth, P. S. et al., *Canadian J. of Biochemistry* vol. 56 (1978), pp. 457–461.
Adams, G. E. et al., *The Lancet*, Jan. 1976, pp. 186–188.
Cheeseman et al., *Advances in Heterocyclic Chem.* vol. 14, Achademic Press, New York (1973), pp. 156, 157, 163.
Olive, Peggy, *Cancer Research*, vol 39 (1979), pp. 4512–4515.

*Primary Examiner*—Donald G. Daus
*Assistant Examiner*—G. Hendricks
*Attorney, Agent, or Firm*—Thomas E. Arther; Mario A. Monaco

[57] ABSTRACT

Di(alkylamino) derivatives of chloronitropyrazines are prepared from dichloronitropyrazinamine by diazotization of the amine followed by halogen exchange to produce an intermediate dichloro-halo nitropyrazine followed by reaction with one or two moles of an alkyl amine to effect replacement of one or two of the pyrazine halogens.

8 Claims, No Drawings

DI(ALKYLAMINO) DERIVATIVES OF CHLORONITROPYRAZINES USEFUL AS ADJUNCTS TO RADIATION THERAPY

This application is a continuation-in-part of application Ser. No. 194,091, filed Oct. 6, 1980, now abandoned.

BACKGROUND OF THE INVENTION

This invention relates to 2,6-disubstituted derivatives of chloronitropyrazines of the formula:

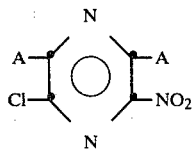

I in which A is defined as an amino substituent wherein at least one of the hydrogens of the amino substituent is replaced by a lower alkyl, an hydroxy substituted lower alkyl, an alkoxy substituted lower alkyl radical. It also relates to the process of preparing such compounds starting with the corresponding 2-halo-5,6-dichloro-3-nitropyrazine by reaction with a selected alkyl amine or substituted alkylamine to replace the 2-halo and 6-chloro substituents. This invention further relates to pharmaceutical composition of such compounds and to methods of treatment comprising administering such compounds to patients undergoing radiation treatment to enhance the effectiveness of such treatment. Thus, such compounds and compositions thereof are used to preferentially sensitize tumor cells to therapeutic radiation and thus increase the effective therapeutic ratio of radiation therapy.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, but are believed to have a more favorable therapeutic ratio.

DETAILED DESCRIPTION OF THE INVENTION

The compositions of the present invention which are useful as radiation sensitizers are di(alkylamino) derivatives of chloronitropyrazine.

A preferred group of such compounds are represented by the following structural formula:

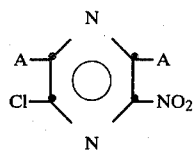

I wherein

A is an amino substituent having at least one of the hydrogens of the amino group replaced by a lower alkyl group, an hydroxy lower alkyl group, a polyhydroxy lower alkyl group, a lower alkoxy lower alkyl group or a polyalkoxy lower alkyl group.

A preferred sub-group of compounds of the present invention are represented by the following structural formula:

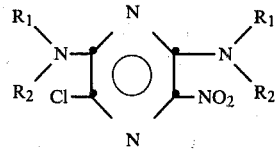

II wherein $R_1$ is $C_{1-6}$ lower alkyl, $C_{1-6}$ branched chain lower alkyl, $C_1-C_6$ Hydroxyalkyl, $C_1-C_6$ polyhydroxyalkyl, $C_1-C_6$ alkoxy alkyl or $C_{1-6}$ polyalkoxy alkyl $R_2$ is hydrogen or $R_1$ In accordance with our invention the starting compound 5,6-dichloro-3-nitropyrazinamine IV, prepared by heating 3-amino-5,6-dichloropyrazincarboxylic acid with a mixture of fuming sulfuric and fuming nitric acids as described in U.S. Ser. No. 194,500, of George D. Hartman filed on Oct. 6, 1980 herewith, is diazotized and exchanged with halogen ion to produce the important novel intermediate 5,6-dichloro-2-halo (Cl, Br, I)-3-nitropyrazine V, which in turn is treated with one or two moles of an alkyl or substituted alkylamine to produce a 2-(alkylamino)-3-chloro-6-halo-5-nitropyrazine VI or 3-chloro-2,6-di(alkylamino)-5-nitropyrazine I as illustrated in the flow sheet below.

FLOW SHEET

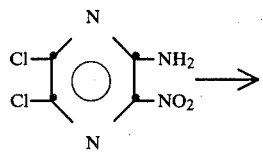

IV

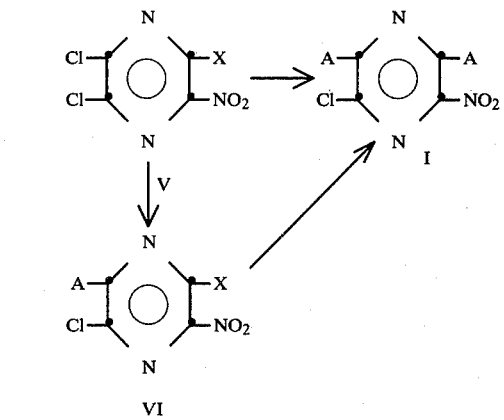

wherein A is defined as hereinabove and X is halogen selected from chloro, bromo or iodo. As shown in the flow sheet, intermediate VI is isolated and reacted if desired, with a different species of alkylamine to produce a 2,6-disubstituted-3-chloro-5-nitropyrazine in which the 2 and 6 substituents may differ from each other.

In carrying out the first step of our process, starting material IV is diazotized and exchanged with halogen ion, e.g. chlorine, bromine, or iodine to produce the desired 2-halo-5,6-dichloro-3-nitropyrazine V. In the preferred instance, compound IV 5,6-dichloro-3-nitropyrazinamine is dissolved in bromoform and to the solution is added at least one mole of an alkyl nitrite compound such as isoamyl nitrite, butyl nitrite, ethyl nitrite and the like. The nitrite reagent is preferably added in approximately an 50–200% molar excess and the reaction mixture is heated at a temperature of 50°–120° for a period of 5–40 hours until the reaction is essentially complete as determined by thin layer chromatography. Following the completion of the reaction the desired product is isolated from the cooled reaction mixture by first evaporation of the excess bromoform solvent in vacuo leaving the crude product as a residual oil which is further purified by chromatography over silica gel.

In further process steps of the present invention, the intermediate V condensed with one or two moles of an alkylamine optionally substituted with one or more hydroxy or alkoxy groups to produce the desired product I in one or more reaction steps with intermediate production, if desired, of the monosubstituted pyrazine VI hereinabove. This reaction which results in the replacement of the 2 & 6 halogen substituents by alkylamino substituents is conducted by mixing together 2-halo-5,6-dichloro-3-nitropyrazine with at least a 100% molar excess of the selected amine compound and maintaining the reaction temperature at 0°–50° for a period of from 0.5 to 16 hours. Preferably the reaction is conducted in the presence of a solvent for the reactants. Suitably, lower aliphatic alcohols such as methanol, ethanol, isopropanol; certain ethers such as tetrahydrofuran; dimethyl formamide, and acetonitrile are useful as solvents for the reaction. Progress of the reaction is conveniently followed by monitoring the disappearance of starting material and appearance of product using thin layer chromatography. Following completion of the reaction the solvent is removed by evaporation in vacuo leaving product as a residual oil which is further purified by trituration with solvents such as ethanol/chloroform mixtures followed by chromatography on silica gel.

The products produced of formula I may be varied by varying the amine reagent. Thus for example, reaction of 2-bromo-5,6-dichloronitropyrazine with one or two moles of selected amine reagent produces the corresponding nitropyrazine in which the 6-chloro and/or the 2-bromo substituent are exchanged by an amino substituent.

The method of treatment of human patients or domestic animals undergoing radiation treatment of malignant disease processes employs the compounds of the present invention in pharmaceutical compositions that are administered orally or parenterally, preferably intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface approximately equivalent to a dosage of 6 to 100 mg/kg of patient body weight as set forth in the "Nelson Textbook of Pediatrics" Eleventh Edition (1979) p. 31, edited by Vaughan, McKay, Behrman, and Nelson.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each suceeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs are preferred.

Capsules or tablets containing from 25, 50, 100 or 500 mg of drug/capsule or tablets are satisfactory for use in the method of treatment of our invention. For tablets or capsules the substantially pure compound may be combined with a pharmaceutically acceptable solid diluent or in the case of capsules filled directly into an appropriately sized capsule.

The following examples are intended to illustrate but do not limit the process of preparation, product, compositions, or method of treatment aspects of the invention.

PREPARATION OF STARTING MATERIAL

Preparation of 5,6-dichloro-3-nitropyrazinamine (II)

To a 450 ml concentrated sulfuric acid cooled to 10 is added 50.0 g (0.2 m) 3-amino-5,6-dichloropyrazine carboxylic acid. To this solution cooled to 0°–5°, is added a cold solution of 15 ml fuming sulfuric acid in 15 ml fuming nitric acid dropwise over 15 minutes. The reaction mixture is stirred at 0°–5° for 2 hours and then at ambient temperature for 2 hours. The reaction mixture is the poured onto ice and the yellow solid is collected. This solid is taken up in ethyl acetate, and then washed twice with saturated sodium carbonate solution and then the solution is filtered through a pad of silica gel. The resulting solution is evaporated in vacuo to afford 35 g of 5,6-dichloro-3-nitropyrazinamine, m.p. 169°–170°.

EXAMPLE 1

2,2'-[(3-chloro-5-nitropyrazin-2,6-yl)diamino]diethanol

STEP A: 2-Bromo-5,6-dichloronitropyrazine

To 4.8 g isoamylnitrite in 150 ml bromoform heated to 95°–100° is added portionwise 5.0 g 5,6-dichloro-3-nitro-pyrazinamine. The reaction mixture is heated at reflux for 18 hours. After cooling, the bromoform is removed in vacuo to give an oil which is chromatographed on silica gel. The initial component to elute is 5,6-dichloro-2-bromonitropyrazine, which is obtained (2.6 g) as a viscous oil.

STEP B: Preparation of 2,2'-[(3-chloro-5-nitropyrazin-2,6-yl)diamino]diethanol

To a solution of 1.0 g 2-bromo-5,6-dichloronitropyrazine in 10 ml isopropanol at 0°–10° is added 0.72 g triethylamine and then 0.44 g 2-aminoethanol. The reaction mixture is stirred at 0°–10° for 0.5 hour and then at room temperature for 0.5 hour. The solvent is then removed in vacuo and the residue triturated with ethanol/chloroform solution to afford a yellow solid which is collected by filtration. This solid is chromatographed on silica gel and the initial compound to elute is 2,2'-[(3-chloro-5-nitropyrazin-2,6-yl)diamino] diethanol, 0.5 g, mp. 148°–150°.

STEP B₁:
2-[(6-Bromo-3-chloro-5-nitropyrazin-2-yl)amino]ethanol

To 1.8 g of 2-bromo-5,6-dichloronitropyrazine in 10 ml isopropanol at 0°–10° is added 0.6 g triethylamine and then 0.31 g ethanolamine. The reaction mixture is stirred at 0°–10° for 0.5 hour and then at room temperature for 15 minutes. The solvent is then removed in vacuo and the resulting oil chromatographed on silica gel with elution by 2% methanol/chloroform. The desired product is collected as a clear oil, identity confirmed by mass spectral analysis. This oil is treated with 0.31 g of ethanolamine and 0.6 g of triethylamine to form 2,2'-[(3-chloro-5-nitropyrazin-2,6-yl)diamino] diethanol.

Employing the procedure substantially as described in Example 1B but employing in Step B the appropriate reagent, there is produced the product shown:

EXAMPLE 2

| REAGENT | PRODUCT |
| --- | --- |
| 3-amino-1,2-propanediol | 3-chloro-2,6-di(2,3-dihydroxypropylamino)-5-nitropyrazine |

EXAMPLE 3

| REAGENT | PRODUCT |
| --- | --- |
| Diethylamine | 3-chloro-2,6-diethylamino 5-nitropyrazine |

EXAMPLE 4

| Tablet Formulation | |
| --- | --- |
| Ingredients | Amount |
| Product of Example 1, 2 or 3 | 25 mg |
| Calcium phosphate | 120 mg |
| Lactose | 50 mg |
| Starch | 23 mg |
| Magnesium Stearate | 1 mg |

EXAMPLE 5

| Injectable Solution | |
| --- | --- |
| Ingredients | Amount |
| Product of Example 1, 2 or 3 | 1 mg |
| Sodium chloride | 9 mg |
| Distilled Water q.s. | 1.0 ml |

What is claimed is:
1. A compound of the formula:

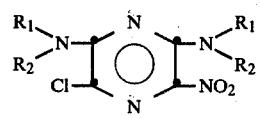

wherein
$R_1$ is $C_1$–$C_6$ hydroxyalkyl, $C_1$–$C_6$ dihydroxyalkyl, $C_1$–$C_6$ alkoxy alkyl and
$R_2$ is hydrogen or $R_1$.

2. A compound of the formula:

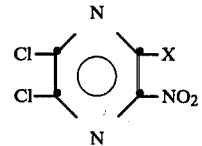

wherein X is defined as chloro, bromo or iodo.

3. A compound according to claim 1 which is selected from 2,2'-[(3-chloro-5-nitropyrazine-2,6-yl)-diamino]ethanol; 3,chloro-2,6-di-(2,3-dihydroxypropylamino)-5-nitropyrazine.

4. A compound according to claim 2 which is 2-bromo-5,6-dichloronitropyrazine.

5. A compound of the formula:

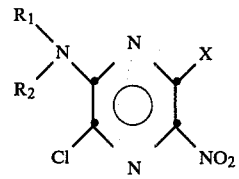

wherein
$R_1$ is $C_1$–$C_6$-hydroxy alkyl, $C_1$–$C_6$-dihydroxy alkyl or $C_1$–$C_6$-alkoxy alkyl; and
$R_2$ is hydrogen or $R_1$,
X is chloro, bromo or iodo.

6. A compound according to claim 5 which is 2-[(6-bromo-3-chloro-5-nitropyrazin-2-yl)amino]-ethanol.

7. A method of enhancing the therapeutic effect of radiation treatment which comprises administering to a patient in need of such radiation treatment an effective sensitizing amount of a compound having the formula:

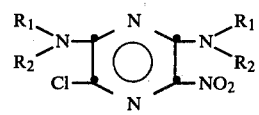

wherein
$R_1$ is $C_{1-6}$ lower alkyl, $C_{1-2}$ branched chain lower alkyl, $C_{1-6}$ hydroxyalkyl, $C_{1-6}$ alkoxy alkyl;
$R_2$ is hydrogen or $R_1$.

8. A composition useful in enhancing the therapeutic effect of radiation treatment comprising a compound of the formula:

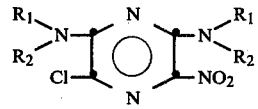

wherein
$R_1$ is $C_{1-6}$ lower alkyl, $C_{1-6}$ branched chain lower alkyl, $C_{1-6}$ hydroxy lower alkyl, $C_{1-6}$ alkoxy alkyl and $R_2$ is hydrogen or $R_1$ and a pharmaceutical carrier.

* * * * *